(12) United States Patent
Jang

(10) Patent No.: US 12,359,364 B2
(45) Date of Patent: Jul. 15, 2025

(54) CLOTHES DRYER USING LED LIGHT SOURCE

(71) Applicant: Kyoung Sook Jang, Siheung-si (KR)

(72) Inventor: Kyoung Sook Jang, Siheung-si (KR)

( * ) Notice: Subject to any disclaimer, the term of this patent is extended or adjusted under 35 U.S.C. 154(b) by 668 days.

(21) Appl. No.: 17/764,679

(22) PCT Filed: Feb. 26, 2021

(86) PCT No.: PCT/KR2021/002442
§ 371 (c)(1),
(2) Date: Mar. 29, 2022

(87) PCT Pub. No.: WO2021/172924
PCT Pub. Date: Sep. 2, 2021

(65) Prior Publication Data
US 2022/0341086 A1   Oct. 27, 2022

(30) Foreign Application Priority Data
Feb. 28, 2020   (KR) .......................... 10-2020-0024744

(51) Int. Cl.
*D06F 58/26* (2006.01)
*A61L 2/10* (2006.01)
(Continued)

(52) U.S. Cl.
CPC ................. *D06F 58/26* (2013.01); *A61L 2/10* (2013.01); *A61L 9/20* (2013.01); *B01D 39/2068* (2013.01);
(Continued)

(58) Field of Classification Search
CPC .......... D06F 58/26; D06F 58/10; D06F 58/22; D06F 34/20; D06F 34/26; D06F 71/29;
(Continued)

(56) References Cited

U.S. PATENT DOCUMENTS 5,546,678 A * 8/1996 Dhaemers ............... F26B 21/02
34/224
5,555,640 A * 9/1996 Ou ......................... F26B 25/066
312/249.9
(Continued)

FOREIGN PATENT DOCUMENTS

KR       10-0370363 B1     1/2003
KR       20-0342334 Y1     2/2004
(Continued)

*Primary Examiner* — Stephen M Gravini
(74) *Attorney, Agent, or Firm* — NKL LAW; Jae Youn Kim

(57) ABSTRACT

A clothes dryer using an LED light source is proposed. Instead of using a heater, a blowing fan, and a heat exchanger, the clothes dryer employs a plurality of LED light source modules provided in a body and efficiently arranged therein and an air circulation structure of an air circulation part having a blowing fan arranged in the inner rear side thereof, and is configured to sterilize air through an air sterilization part, absorb and dry moisture by a ceramic filter, and then finally discharge the air to the outside through an exhaust fan. Therefore, without requiring a separate water discharge treatment process in an existing method, the clothes dryer can achieve efficient drying of clothes and drying of clothes without damage.

7 Claims, 15 Drawing Sheets

(51) Int. Cl.

| | |
|---|---|
| *A61L 9/20* | (2006.01) |
| *B01D 39/20* | (2006.01) |
| *B01D 53/26* | (2006.01) |
| *D06F 34/20* | (2020.01) |
| *D06F 34/26* | (2020.01) |
| *D06F 58/10* | (2006.01) |
| *D06F 58/22* | (2006.01) |
| *D06F 58/38* | (2020.01) |
| *D06F 71/29* | (2006.01) |
| *D06F 103/34* | (2020.01) |
| *D06F 103/40* | (2020.01) |

(52) U.S. Cl.
CPC ........... *B01D 53/266* (2013.01); *D06F 34/20* (2020.02); *D06F 34/26* (2020.02); *D06F 58/10* (2013.01); *D06F 58/22* (2013.01); *D06F 58/38* (2020.02); *D06F 71/29* (2013.01); *D06F 2103/34* (2020.02); *D06F 2103/40* (2020.02)

(58) Field of Classification Search
CPC .. D06F 2103/34; D06F 2103/40; A61L 21/10; A61L 9/20; B01D 53/266; B01D 39/2068
USPC ............................................................ 34/90
See application file for complete search history.

(56) References Cited

U.S. PATENT DOCUMENTS

| | | | | |
|---|---|---|---|---|
| 9,310,088 | B2* | 4/2016 | Melikov | ................ G16H 50/80 |
| 9,557,106 | B2* | 1/2017 | Stewart | .................... F26B 3/28 |
| 10,842,897 | B2* | 11/2020 | Schwartz | ............... A61L 2/202 |
| 10,935,313 | B2* | 3/2021 | Stewart | .................... D06F 59/04 |
| 11,350,799 | B2* | 6/2022 | Yang | .................... A47K 10/48 |
| 12,012,689 | B2* | 6/2024 | Oak | ........................ D06F 58/24 |
| 12,232,683 | B2* | 2/2025 | Jung | ........................ A61L 2/07 |
| 2022/0341086 | A1* | 10/2022 | Jang | .................... B01D 53/266 |
| 2022/0347333 | A1* | 11/2022 | Monaco | ................ D06F 58/10 |
| 2023/0212814 | A1* | 7/2023 | Kim | ........................ D06F 58/22 |
| | | | | 34/389 |
| 2024/0011691 | A1* | 1/2024 | Kim | .................... F25B 49/025 |
| 2024/0263380 | A1* | 8/2024 | Schäfer | ............. B01D 53/8696 |

FOREIGN PATENT DOCUMENTS

| | | | | |
|---|---|---|---|---|
| KR | 20-2007-0001318 U | 12/2007 | | |
| KR | 10-2012-0133473 A | 12/2012 | | |
| KR | 10-1565953 B1 | 11/2015 | | |
| KR | 10-2020-0005116 A | 1/2020 | | |
| KR | 102344874 B1 * | 12/2021 | | |
| WO | WO-2021172924 A2 * | 9/2021 | ............... | A61L 2/10 |
| WO | WO-2022214481 A1 * | 10/2022 | ............... | A61L 9/205 |

\* cited by examiner

CLOTHES DRYER USING LED LIGHT SOURCE

TECHNICAL FIELD

The present invention relates to a clothes dryer using an LED light source, and more particularly, to a clothes dryer using an LED light source which may achieve efficient drying of clothes without damage to the clothes through efficient arrangement of LED light source modules, internal air circulation and discharge structures, and humidity control without water discharge rather than through a general drying method using a heater, an air blowing fan and a heat exchanger.

BACKGROUND ART

In general, a clothes dryer is an apparatus which removes remaining moisture from clothes after washing, and is included in a general washing machine so as to dry washed clothes after spin-drying.

Drying of laundry, which has been spin-dried, is performed in the drum of the washing machine or is performed by the clothes dryer provided separately from the washing machine and, in order to more rapidly dry the laundry, the laundry is dried within a given time through supply of heat using a heater and supply of air using an air blowing fan.

During drying of clothes mainly using the washing machine, the clothes are dried in the state in which various types of laundry are mixed in the drum, and thus, there are drawbacks, such as a long drying time and generation of wrinkles of the clothes after drying.

On the other hand, during drying of clothes in which the clothes are taken out of the washing machine, are then put into the clothes dryer and are dried through hot air circulation in the clothes dryer, the drying time, the intensity of hot air, etc. need to be controlled depending on the material of laundry, and thus cause inconvenience in control.

In the above-described drying method, drying of the clothes are performed through an air circulation structure using a compressor and a heat exchanger provided in the clothes dryer, and water collected in a water case disposed under the heat exchanger due to dew concentration caused by driving of the heat exchanger must be removed by withdrawing the water case, or must be discharged to the outside through a separate drain pipe connected to the water case.

Further, in case that water discharge is not properly performed, driving of the clothes dryer may stopped in order to prevent overflow of water from the water case in the driving state of the clothes dryer, and thereby, a reserved drying mode may not be efficiently executed.

Meanwhile, an apparatus for disinfecting clothes using a UV LED is provided, and this apparatus is disclosed in Korean Patent Registration No. 10-1565953 (entitled "Apparatus for Disinfection of Clothing Using UV LED", registered on Oct. 29, 2015, and will be referred to as "Patent Document" hereinafter).

The apparatus disclosed in Patent Document includes a booth configured to accommodate clothes therein and provided with a door installed at one side surface thereof, rod-shaped power connectors installed to traverse the upper region of the inside of the booth, and a hanger formed in a loop shape so as to be held on the power connector and including loop parts to which power is supplied when the hanger is held on the power connector and mount parts extending laterally from the loop parts so that clothes are hung on the mount parts and provided with first UV LED lamps installed thereunder to radiate ultraviolet light of wavelengths having a sterilization function so as to sterilize the inside of the clothes, push buttons pressed by the weight of clothes when the clothes are hung thereon so as to transmit a mounting signal to a controller are installed on the mount parts, the push buttons are pressed and then transmit the mounting signal to the controller and the controller controls the first UV LED lamps to be turned on when the clothes are hung on the mount parts, the push buttons are returned to the original positions thereof and then transmit a separating signal to the controller and the controller controls the first UV LED lamps to be turned off when the clothes are separated from the mount parts, CdS illuminance sensors are further installed on the mount parts, the CdS illuminance sensors sense reduction in illuminance around the mount parts and then transmit the mounting signal to the controller and the controller controls the first UV LED lamps to be turned on when the clothes are hung on the mount parts, the CdS illuminance sensors sense increase in illuminance around the mount parts and then transmit the separating signal to the controller and the controller controls the first UV LED lamps to be turned off when the clothes are separated from the mount parts, the power connectors are provided in a pair of positive (+) and negative (−) poles, the loop parts of the hanger are provided in a pair of positive (+) and negative (−) poles facing each other, the first UV LED lamps are in a standby state when the hanger is held on the power connectors such that the loop parts serving as the positive (+) and negative (−) poles respectively correspond to the power connectors serving as the positive (+) and negative (−) poles, and the first UV LED lamps start to be operated by current when push buttons or the CdS illuminance sensors sense that clothes are hung on the hanger.

In such a manner, when clothes are hung on the hanger, hanging of the clothes on the hanger is detected and then ultraviolet light of wavelengths having the sterilization function is radiated so as to disinfect the clothes, when an object approaches the apparatus or the door of the apparatus is open, approach of the object or opening of the door is detected and then radiation of ultraviolet light is stopped so as to protect the human body from ultraviolet light, the UV LED lamps having low power consumption are used, hanging of clothes on the hanger and separation of the clothes from the hanger are detected and controlled, and thus efficient use of energy may be facilitated.

However, this Patent Document limits a light source using UV LEDs to a function of disinfecting clothes, and provides only technology in which clothes worn by a customer as clothes for going out are hung on the hanger for a moment and are thus sterilized and treated using UV-C light having wavelengths of 200 nm to 280 nm radiated from the UV LED lamps, and therefore, this technology is insufficient to dry clothes.

DISCLOSURE OF INVENTION

Technical Problem

Therefore, the present invention has been made in view of the above problems, and it is an object of the present invention to provide a clothes dryer using an LED light source which may efficiently dry clothes without damage to the clothes through efficient arrangement of LED light source modules, internal air circulation and discharge structures, and humidity control without water discharge rather than through a general drying method using a heater, an air blowing fan and a heat exchanger.

Technical Solution

In accordance with the present invention, the above and other objects can be accomplished by the provision of a clothes dryer using an LED light source, including a main body formed as a rectangular body, and provided with a hinged door provided on a front surface of the main body, a laundry drying compartment having hanger rods provided horizontally in upper and lower portions thereof inside the main body, a light source installation part provided under the laundry driving compartment, and a controller provided on one side of a front surface of the main body, a plurality of LED light source modules installed under the drying compartment and configured to radiate light upwards so as to dry laundry using the radiated light, air circulation parts provided with first passages formed on both sides of an inner rear surface of the drying compartment so as to communicate with the light source installation part, and a plurality of air blowing fans and a plurality of blow holes arranged inside the passages so as to perform air circulation and configured to guide air to an inside of the drying compartment through the light source installation part and the first passages, an air sterilization part provided with a second passage formed between the first passages of the air circulation parts so as to be divided from the first passages by partition walls, a plurality of first through holes provided in the second passage, UV LEDs configured to radiate light to the drying compartment and air introduced thereinto so as to sterilize the air, and a plurality of ceramic filters configured to absorb moisture from the introduced air, the UV LEDs and the ceramic filters being installed at positions of the first through holes inside the air sterilization part, and an air discharge part provided with a third passage configured to extend from an upper part of the second passage to an inside of a ceiling at an upper part of the drying compartment, a plurality of second through holes formed in the third passage so as to communicate with the drying compartment, a humidity sensor configured to measure humidity inside the second passage and the drying compartment, illumination lamps configured to illuminate the inside of the drying compartment depending on opening and closing of the hinged door, the humidity sensor and the illumination lamps being provided on the second through holes, a plurality of third through holes formed through one side of the third passage, and an exhaust fan provided on the third through holes so as to discharge air to an outside of the main body.

The plurality of ceramic filters may be provided in a form of a hollow block so as to have a moisture absorption area, and may be arranged and fixedly installed at regular intervals by brackets.

A support tray provided with a perforated part formed therethrough so as to transmit light may be detachably installed on the LED light source modules.

The air blowing fans provided in the first passages may blow air to the inside of the drying compartment by controlling a strength of a current of air under control of the controller.

Each of the plurality of LED light source modules may include a radial heat sink, and a radiation fan provided under the heat sink and configured to blow air so as to radiate heat generated from the heat sink.

A thin stainless steel plate for heat reflection may be added to the inside of the drying compartment of the main body and an inner surface of the hinged door.

A trouser ironing plate formed of stainless steel to iron trousers may be rotatably provided on a rear surface of the hinged door.

Advantageous Effects

A clothes dryer using an LED light source according to the present invention sterilizes air through an air sterilization part in addition to efficient arrangement of a plurality of LED light source modules provided in a main body and the air circulation structure of air circulation parts provided with air blowing fans arranged in the inner rear side of the main body, absorbs and dries moisture through ceramic filters, and then finally discharges air to the outside through an exhaust fan, thereby not requiring a separate water discharge process which was conventionally performed, and efficiently drying clothes without damage to the clothes.

Further, the clothes dryer according to the present invention guides heat conducted to heat sinks of the LED light source modules to first passages of air circulation parts through driving of radiation fans, allows air introduced into the first passages to be naturally introduced into the first passages together with external air from below the main body, and allows hot air to be introduced into a drying compartment through air blowing fans disposed at the same interval in the first passages so that the inhaled hot air is recirculated into the drying compartment through the blow holes, thereby being capable of maximizing drying of laundry.

In addition, the clothes dryer according to the present invention repeats a process of inhaling humid air generated due to drying of the laundry from the hollows and the surfaces of the ceramic filters, sufficiently absorbing moisture from the humid air while passing through the ceramic filters, and drying the moisture using hot air passing by the ceramic filters, and may thus dry clothes through warm air circulation without requiring to separately collect condensate water generated via a heat exchanger like a conventional dehumidification function, thereby solving inconvenience due to use of an additional apparatus configured to collect the condensate water and an additional operation of discharging the condensate water.

Moreover, the clothes dryer according to the present invention allows a plurality of air blowing fans in the air circulation parts to be driven at a low speed so as to form an air flow, shakes off clothes through control of the strength of the current of air blown by the air blowing fans, and thereby, may not only increase the drying effect but also efficiently remove dust from clothes worn by a customer while going out.

BEST MODE FOR CARRYING OUT THE INVENTION

Figure 1:
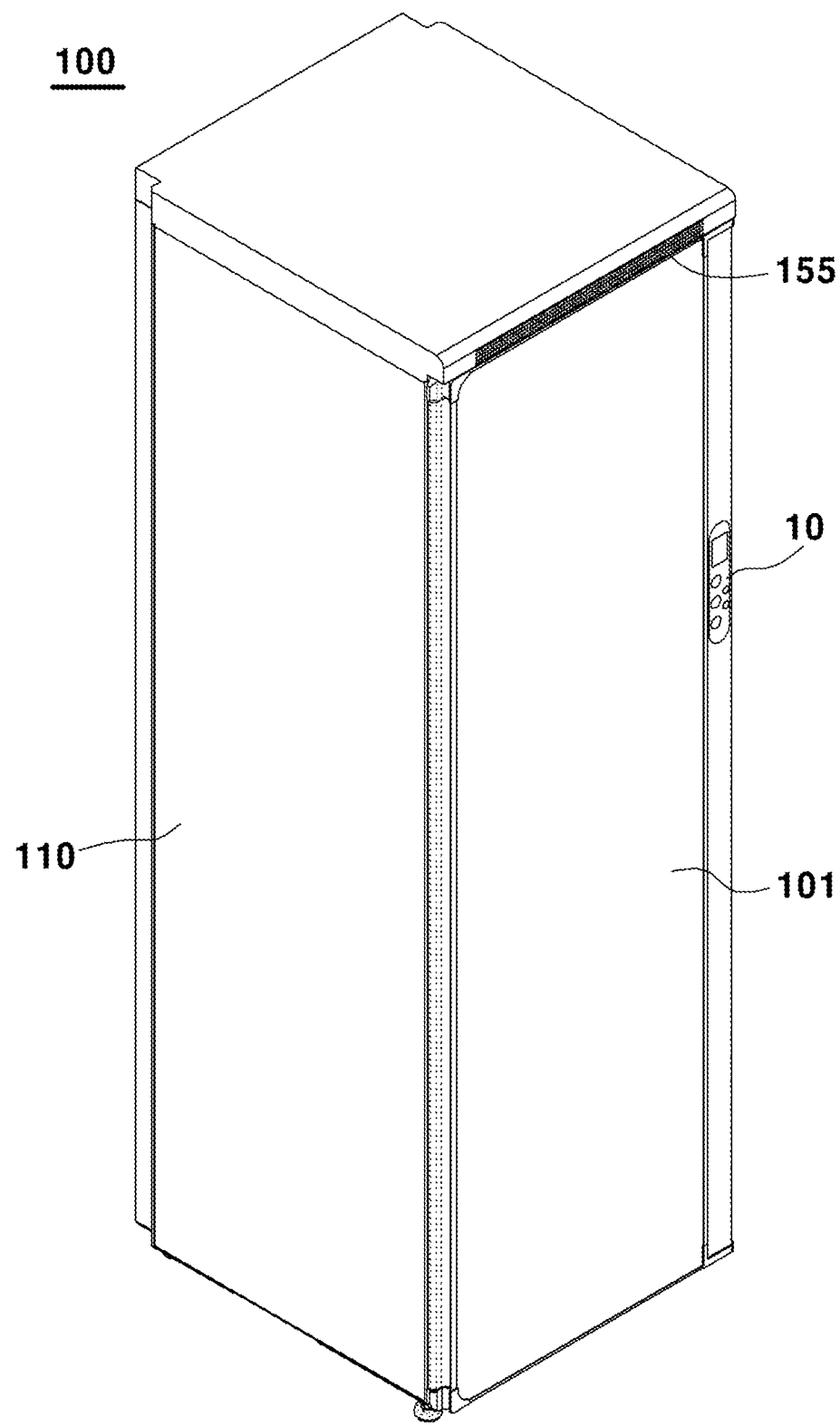
FIG. 1 is a perspective view illustrating a clothes dryer according to the present invention.
Figure 2:
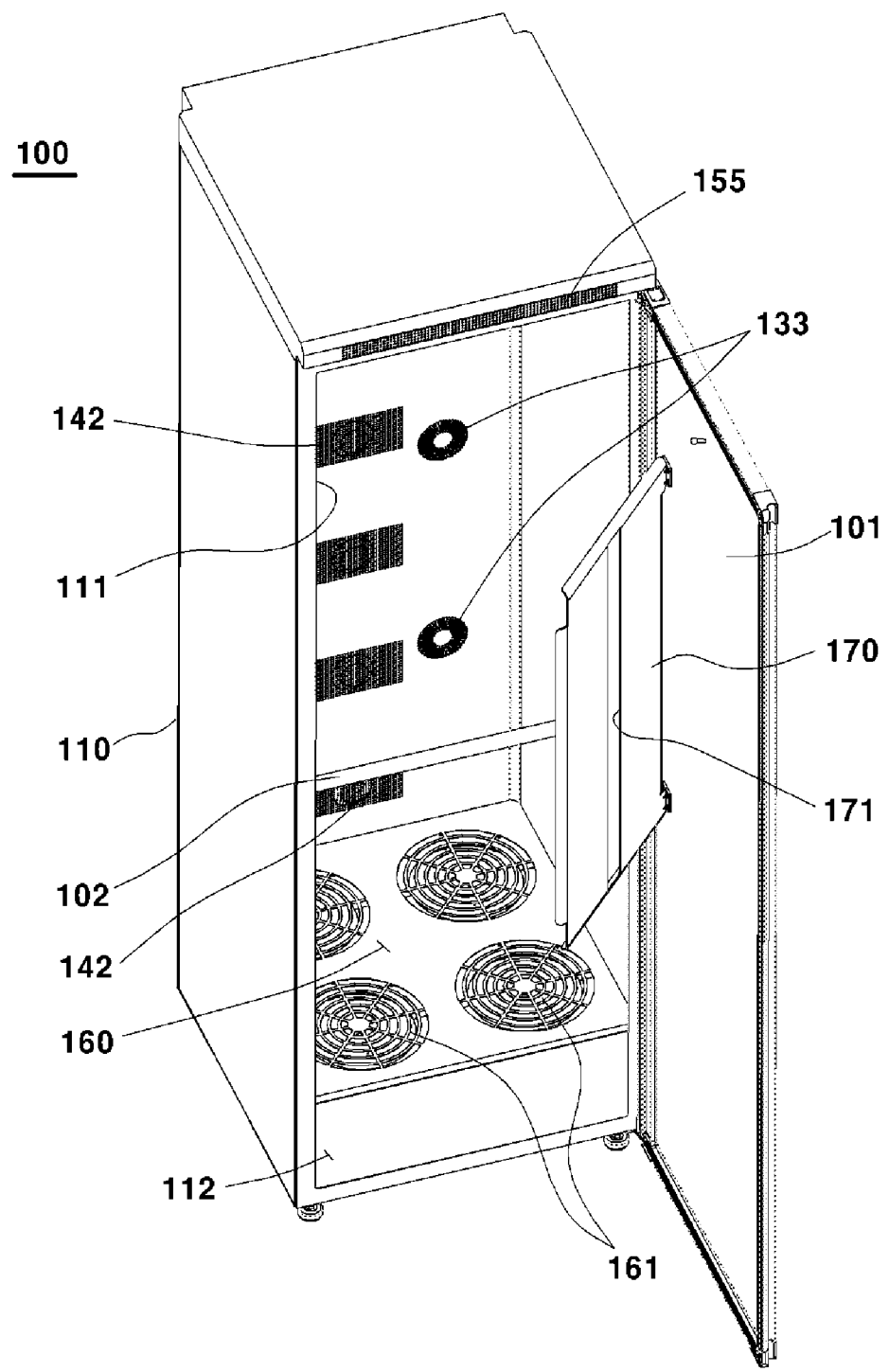
FIG. 2 is a perspective view illustrating the state of the clothes dryer according to the present invention in which a front hinged door is open.
Figure 3:
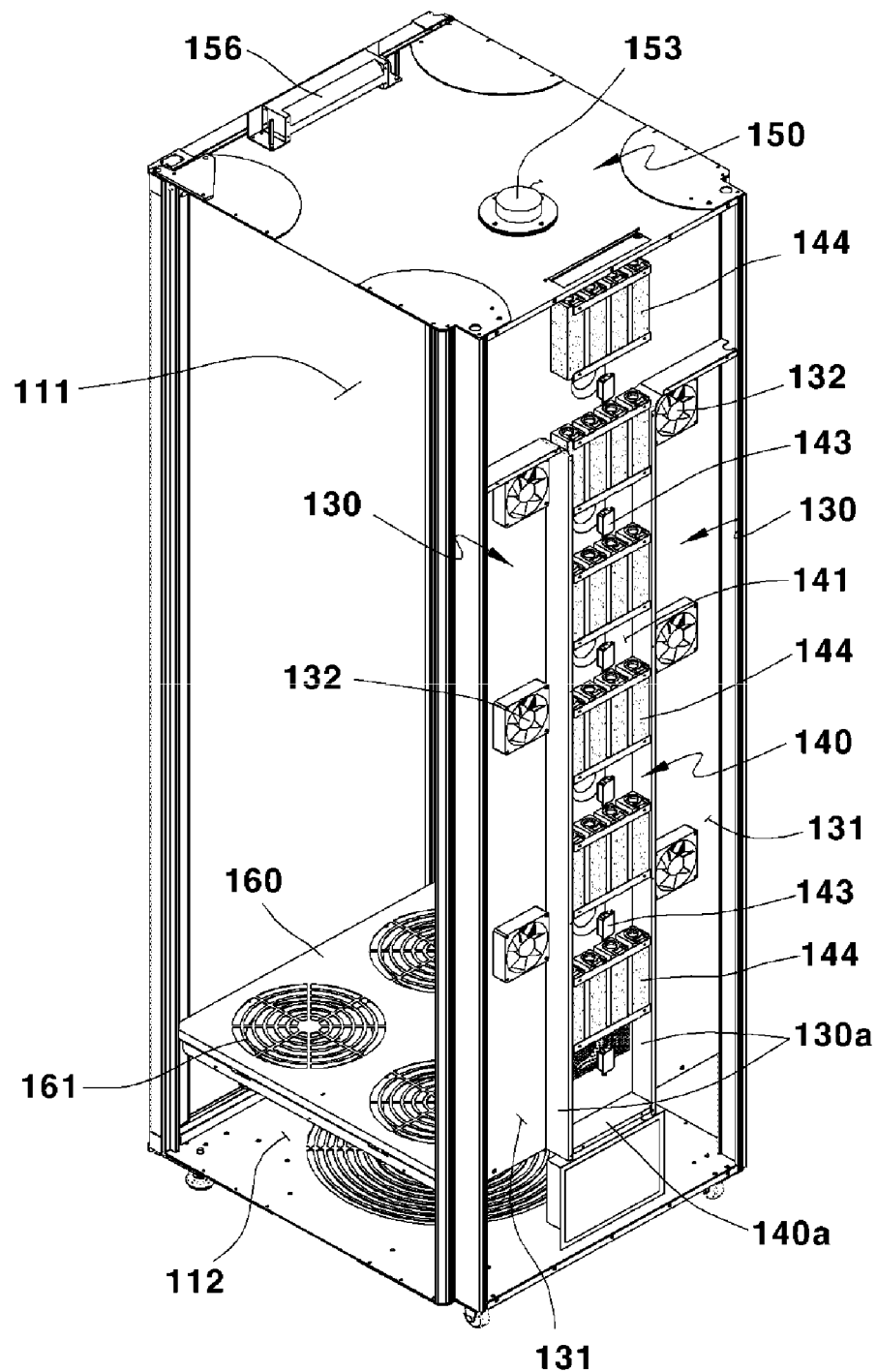
FIG. 3 is a rear perspective view illustrating the state of the clothes dryer according to the present invention in which an outer panel is removed.
Figure 4:
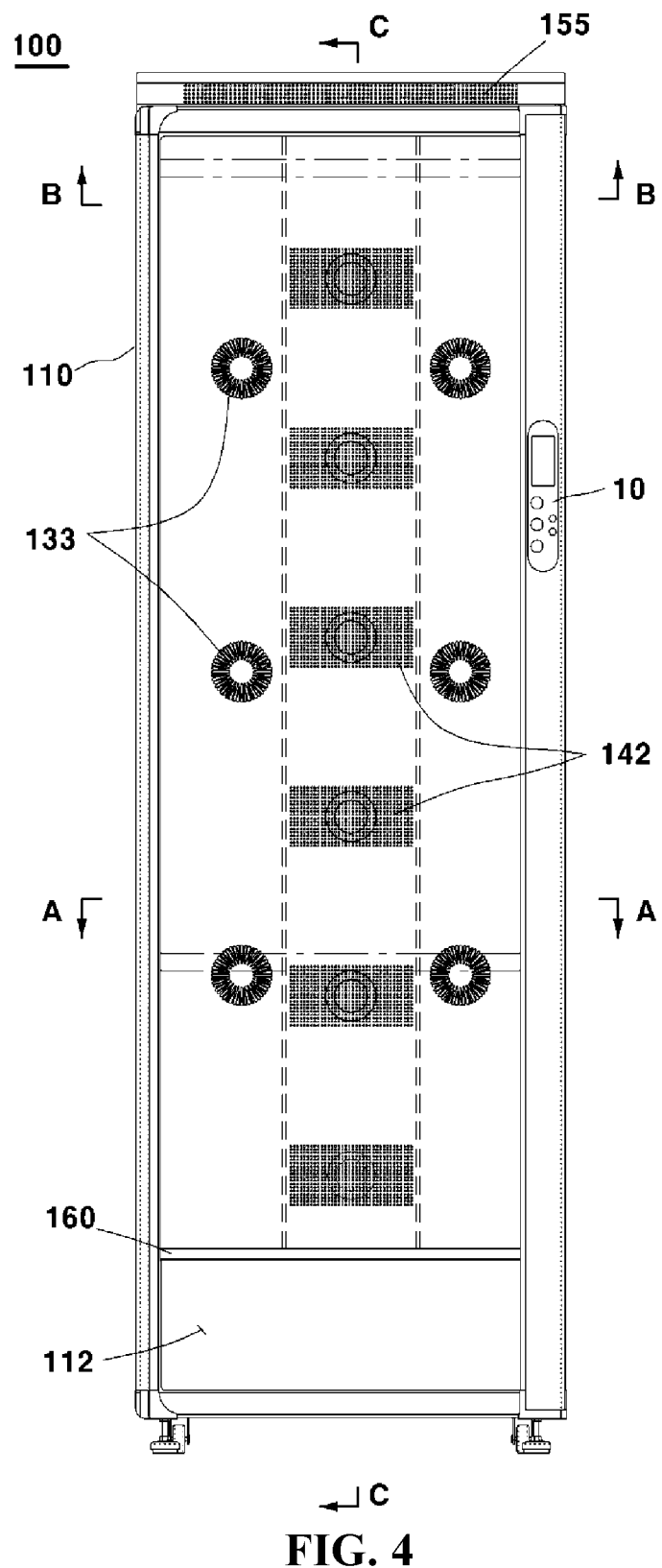
FIG. 4 is a front view illustrating the state of the clothes dryer according to the present invention in which the front hinged door is removed.
Figure 5:
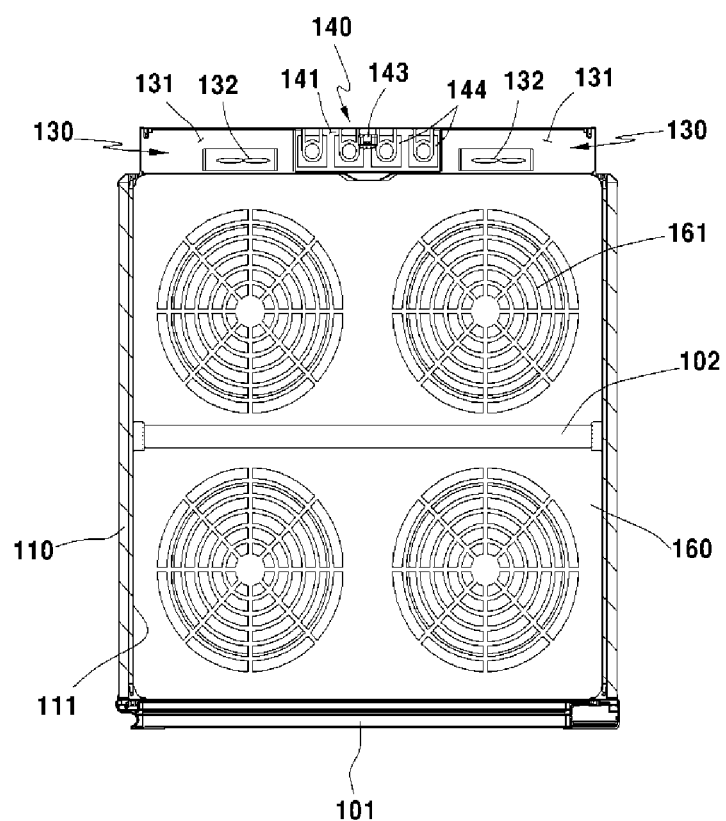
FIG. 5 is a cross-sectional view taken along line A-A of FIG. 4.
Figure 6:
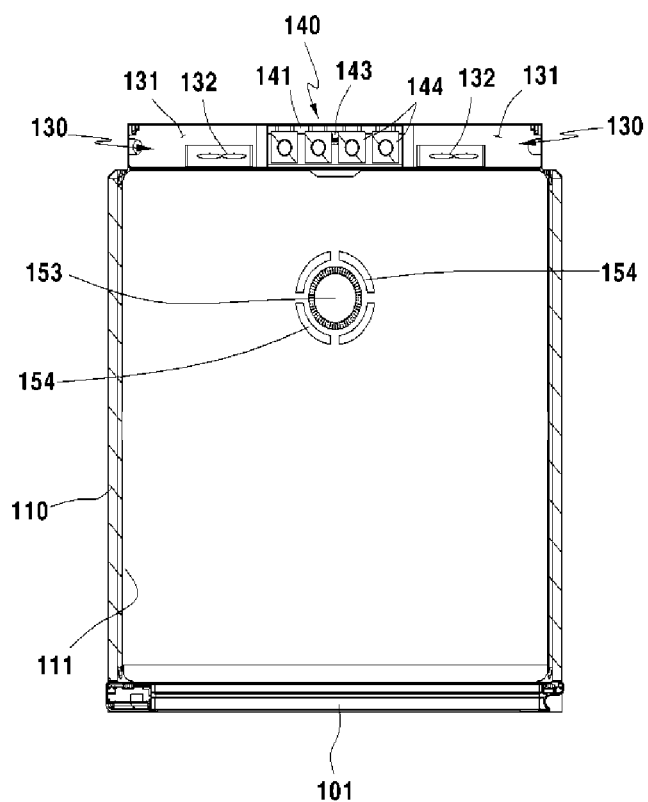
FIG. 6 is a cross-sectional view taken along line B-B of FIG. 4.
Figure 7:
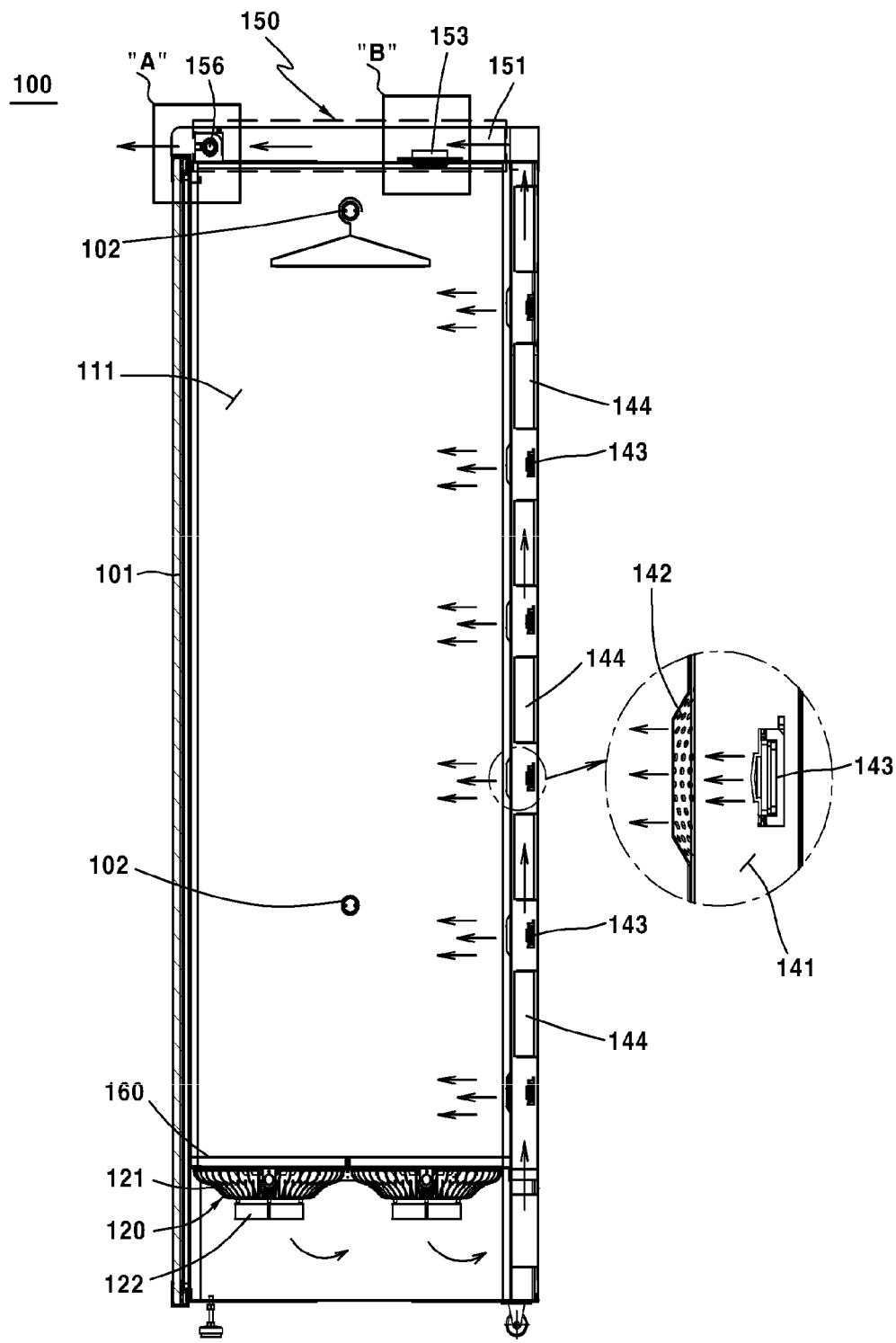
FIG. 7 is a cross-sectional view taken along line C-C of FIG. 4.
Figure 8:
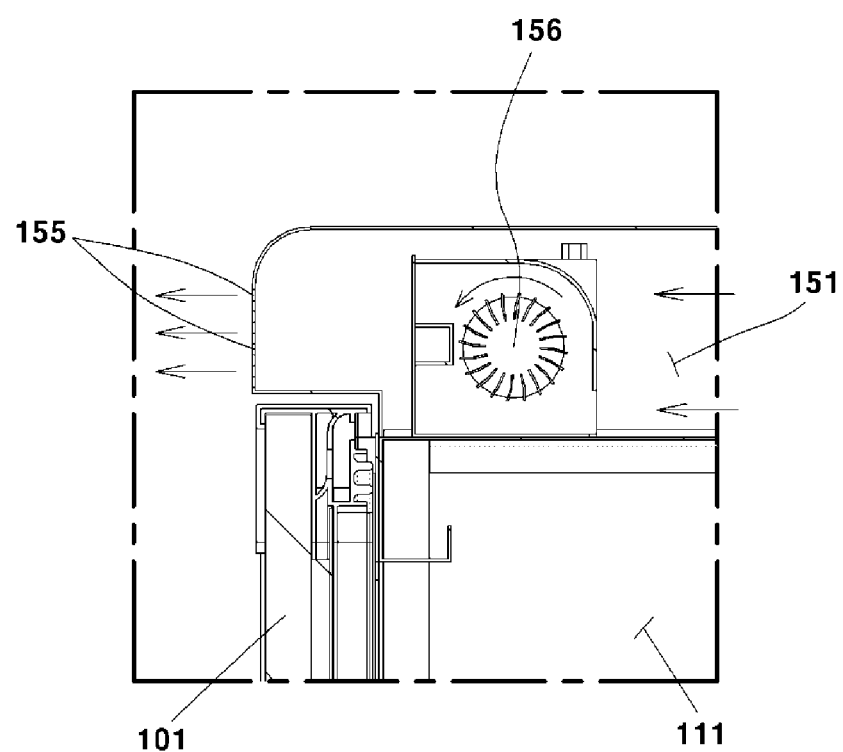
FIG. 8 is an enlarged view of a portion A of FIG. 7.
Figure 9:
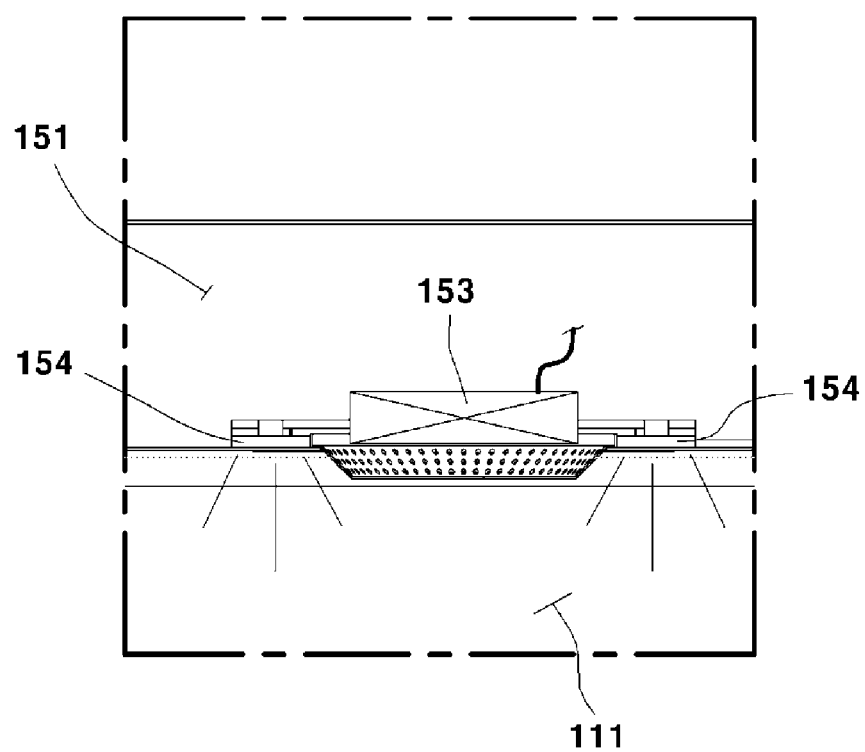
FIG. 9 is an enlarged view of a portion B of FIG. 7.

Hereinafter, reference will now be made in detail to preferred embodiments of the present invention, examples of which are illustrated in the accompanying drawings.

A clothes dryer 100 according to the present invention will be described as follows with reference to FIGS. 1 to 15.

The clothes dryer 100 according to the present invention includes a main body 110, LED light source modules 120, air circulation parts 130, an air sterilization part 140 and an air discharge part 150.

The main body 110 is formed as a rectangular body, a hinged door 101 is provided on the front surface of the main body 100, a laundry drying compartment 111 having hanger rods 102 arranged horizontally in the upper and lower portions thereof is provided inside the main body 110, a light source installation part 112 is provided under the laundry driving compartment 111, and a controller 10 is provided on one side of the front surface of the main body 110.

A trouser ironing plate 170 formed of stainless steel to iron trousers is rotatably provided on the rear surface of the hinged door 101. The trouser ironing plate has a long hole 171 formed in the length direction thereof in the midsection thereof, and the hole hole 171 guides sewing lines of the side surfaces of trousers so as to exhibit a trouser ironing effect due to a thickness difference between the sewing lines when the trousers are pressed using the trouser ironing plate.

Further, a hook part for hangers, configured such that a hanger on which trousers are hung is hung on the hook part, protrude from the upper portion of the rear surface of the hinged door on which the trouser ironing plate is installed.

The inside of the drying compartment 111 of the main body 110 and the inner surface of the hinged door 101 are formed through combination of panels to which a thin stainless steel plate for heat reflection is added.

Figure 10:
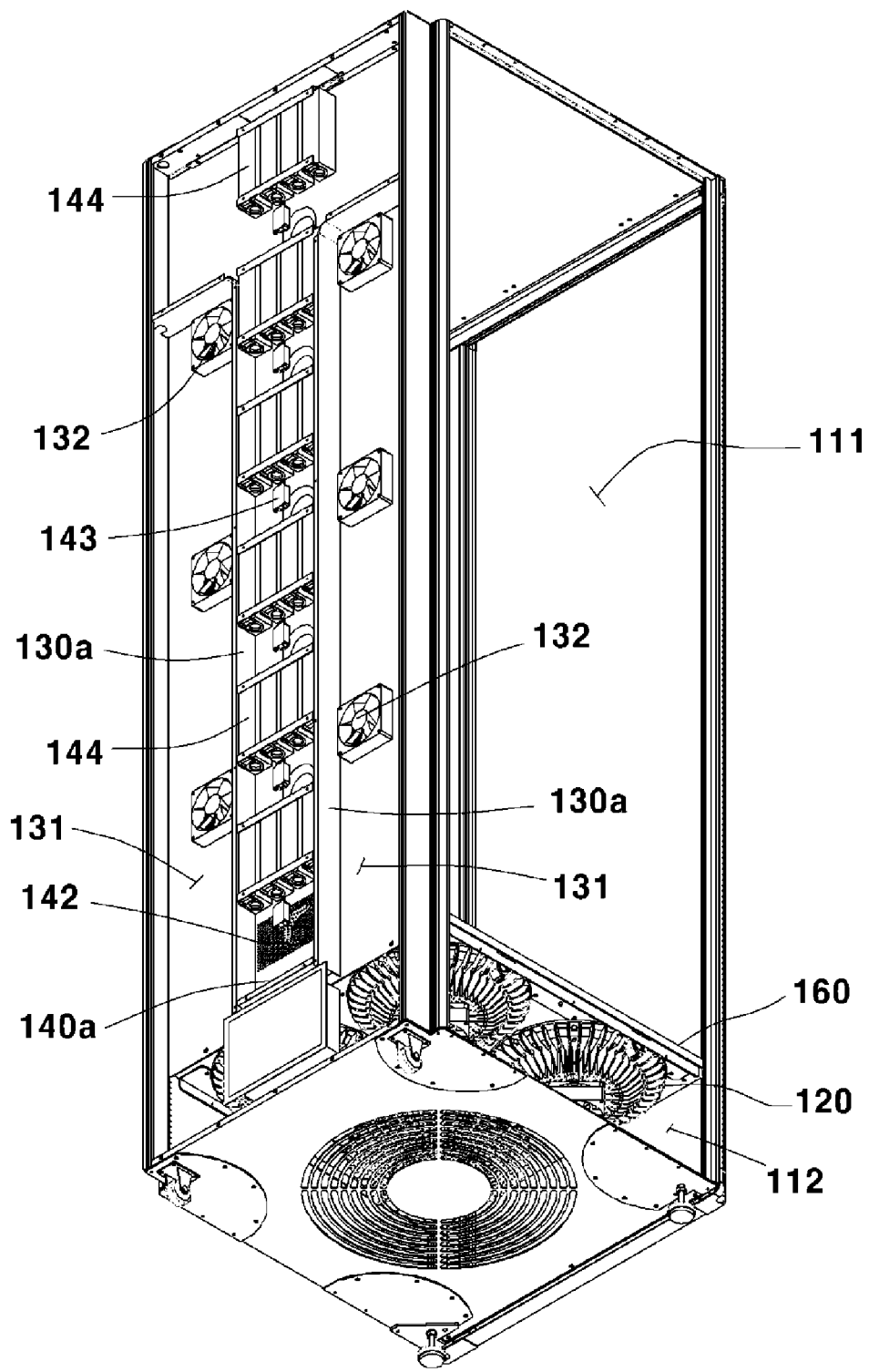
FIG. 10 is a perspective view illustrating air circulation parts and an air sterilization part according to the present invention.
Figure 11:
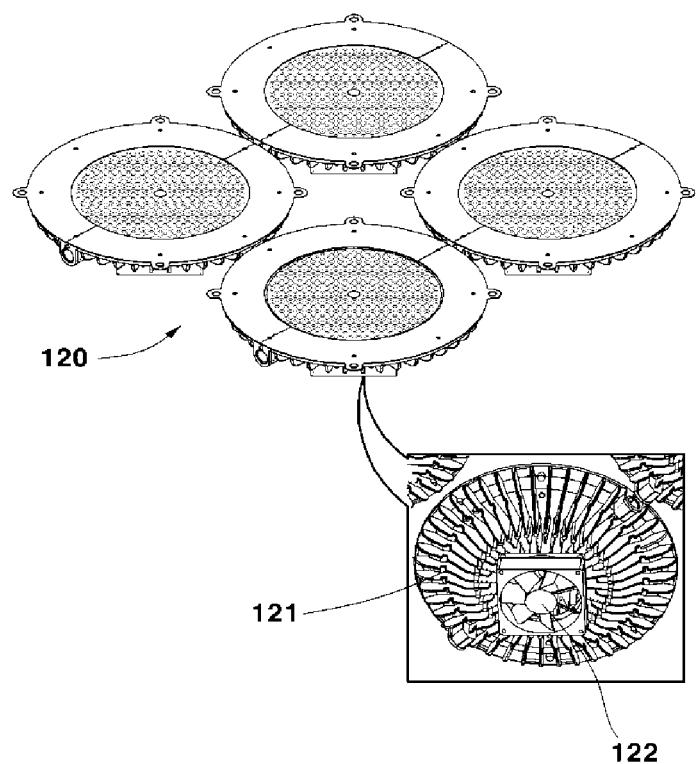
FIG. 11 is a rear view illustrating an air flow in the air circulation parts and the air sterilization part of FIG. 10 as an example.
Figure 12:
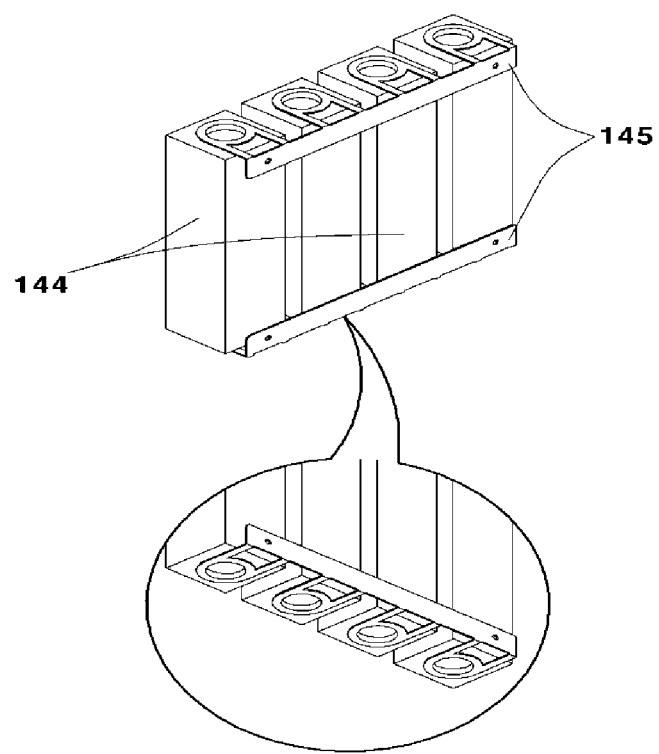
FIG. 12 is a perspective view illustrating LED light source modules according to the present invention.
Figure 13:
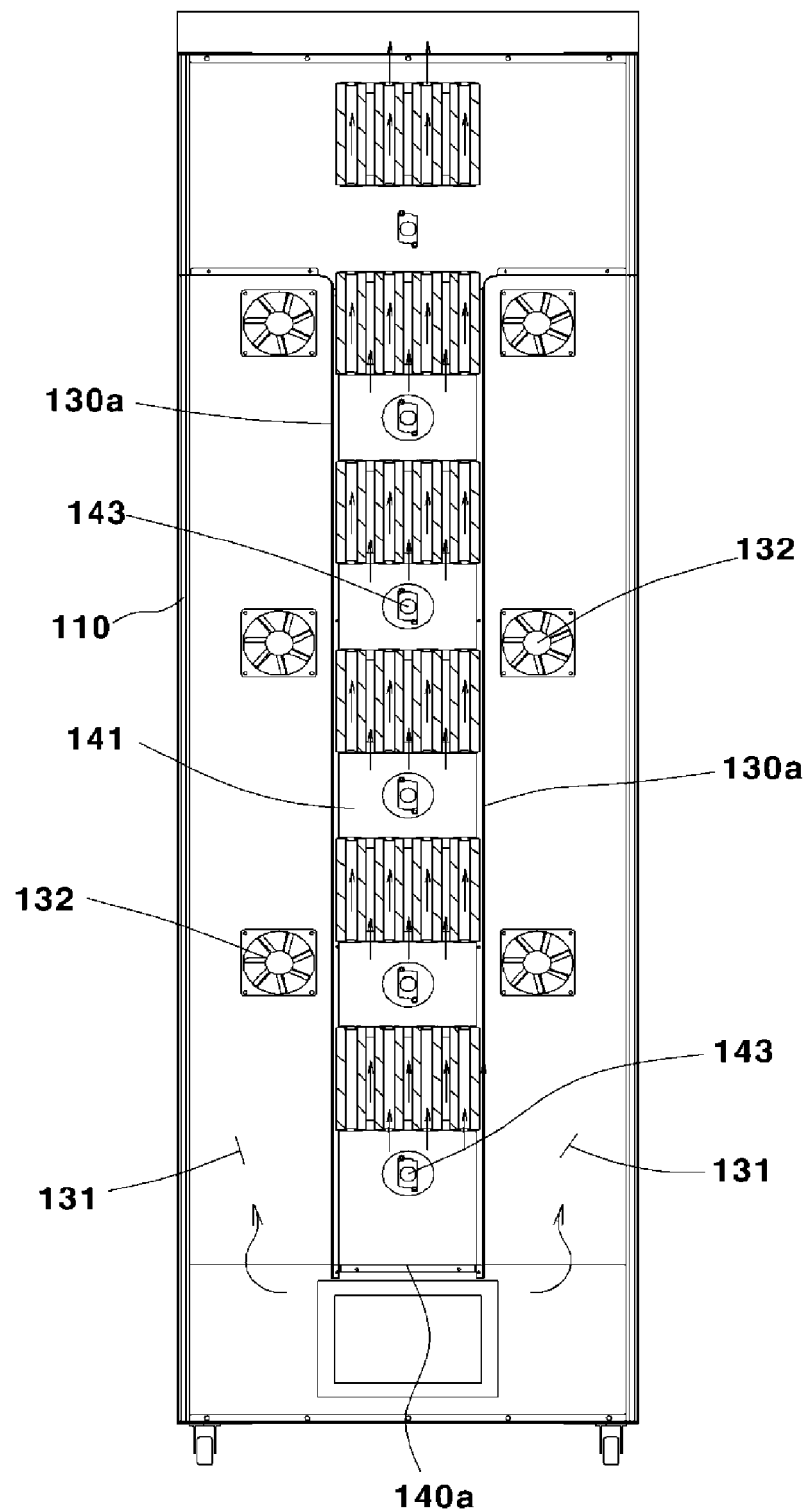
FIG. 13 is a perspective view illustrating a ceramic filter according to the present invention.
Figure 14:
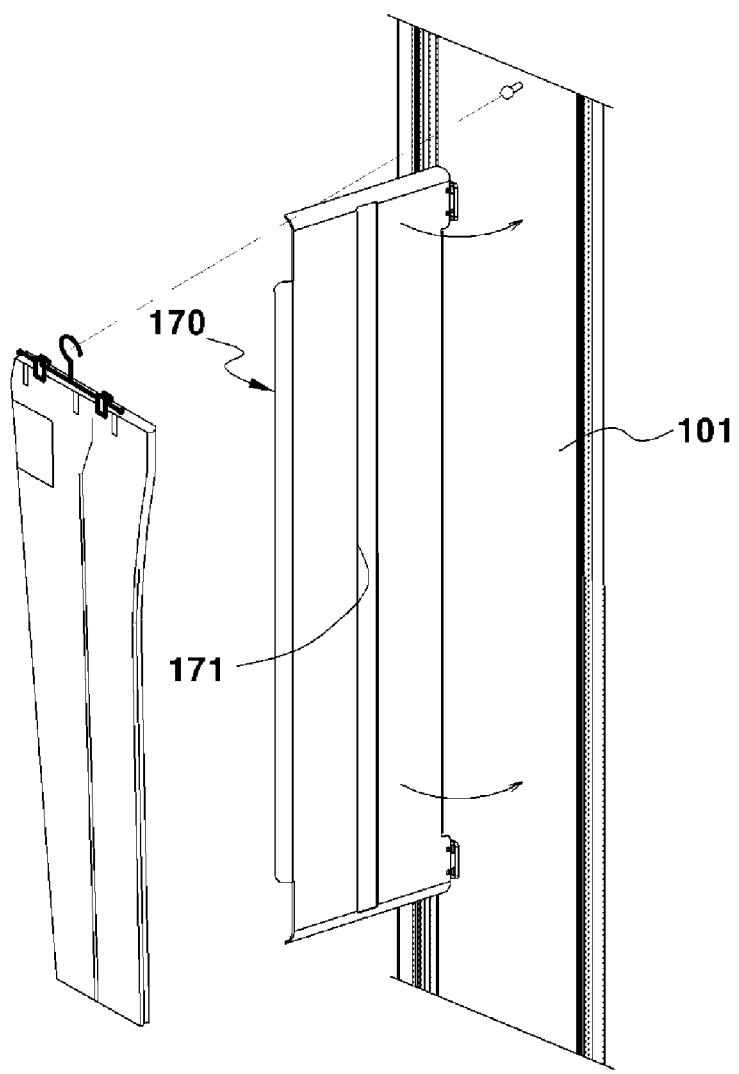
FIG. 14 is a perspective view illustrating a trouser ironing plate provide on the hinged door according to the present invention.
Figure 15:
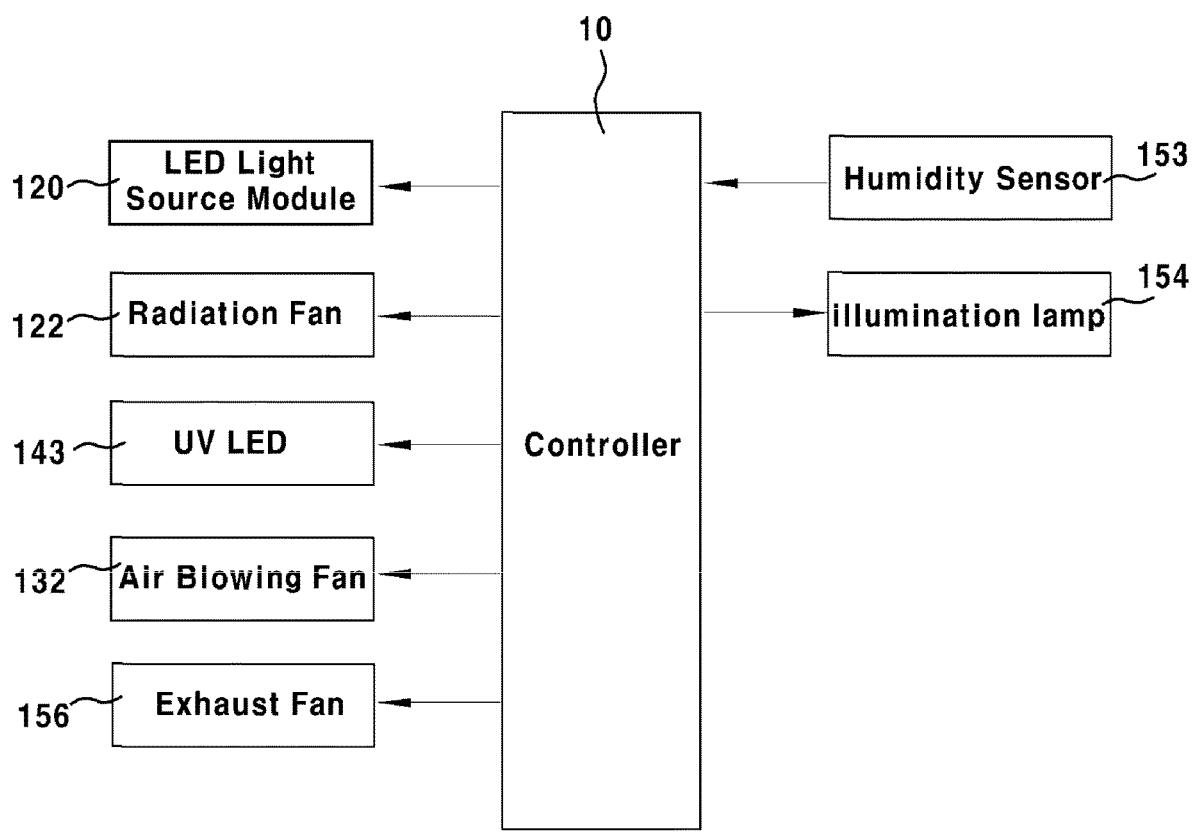
FIG. 15 is a block diagram showing a connection state between elements and a controller according to the present invention.

The main body 110 is formed in a type into which external air naturally flows from below, and a perforated plate is provided on the bottom surface of the main body 110 such that external air flows into the light source installation part through the perforated plate, as shown in FIG. 10.

The LED light source modules 120 are provided in plural, four LED light source modules 120 are installed in the drawings, and the LED light source modules 120 radiates light having a color temperature of 5700 k corresponding to the wavelengths of sunlight and thus sterilizes and dries clothes in the drying compartment through heat and a sterilizing effect due to the radiated light, and is arranged so as to radiate heat in the upward direction from below the drying compartment 111 of the main body 110.

A support tray 160 provided with a perforated part 161 formed therethrough so as to transmit light is detachably installed on the LED light source modules 120. The support tray 160 prevents laundry from coming into contact with the LED light source modules, and allows shoes, bags, etc. to be placed thereon so as to be dried.

Each of the plurality of LED light source modules 120 includes a plurality of LEDs provided on a circular printed circuit board, a radial heat sink 121 configured to surround the LEDs, and a radiation fan 122 provided under the heat sink 121 and configured to radiate heat generated from the heat sink.

The air circulation parts 130 and the air sterilization part 140 are prepared in separate spaces provided on the inner rear surface of the main body so that respective elements are arranged in the air circulation parts 130 and the air sterilization part 140, the air circulation parts 130 are formed by dividing the inner rear surface of the main body into first passages 131 and a second passage 141 by partition walls 130a, the first passages 131 form the air circulations parts 130 divisionally provided at both sides of the main body, and the second passage 141 forms the air sterilization part 140 located between the first passages 131.

The air circulation parts 130 have the first passages 131 which are formed on both sides of the inner rear surface of the drying compartment 111 and communicate with the light source installation part 112, and a plurality of air blowing fans 132 and a plurality of blow holes 133 for air circulation are arranged in the first passages 131 so as to guide air to the inside of the drying compartment 111 through the light source installation part 112 and the first passages 131.

A sealing plate 140a is installed to close the lower portion of the second passage 141 of the air sterilization part 140, and the second passage 141 is formed between the first passages 131 so as to be divided from the first passages 131 of the air circulation parts 130 by the partition walls. A plurality of first through holes 142 is provided at the same interval in the second passage 141, and UV LEDs 143 which radiate light to the inside of the drying compartment 111 and air introduced thereinto are installed at the positions of the first through holes 142 inside the second passage 141.

Further, a plurality of ceramic filters 144, which absorbs moisture from the air introduced through the first through holes 142, is provided between the UV LEDs 143.

The plurality of ceramic filters 144 is provided in the form of a hollow block so as to have a moisture absorption area, and is arranged and fixedly installed at regular intervals by brackets 145.

The air discharge part 150 includes a third passage 151 extending from the upper part of the second passage 141 to the inside of the ceiling at the upper part of the drying compartment 111, a plurality of second through holes 152 formed in the third passage 151 so as to communicate with the drying compartment 111, a humidity sensor 153 configured to measure humidity inside the second passage 141 and the drying compartment 111, illumination lamps 154 configured to illuminate the inside of the drying compartment depending on opening and closing of the hinged door 101, the humidity sensor 153 and the illumination lamps 154 being provided on the second through holes 152, a plurality of third through holes 155 formed through one side of the third passage 155, and an exhaust fan 156 provided on the third through holes 155 so as to discharge air to the outside of the main body 110.

The air blowing fans 132 provided in the first passages 131 blow air to the inside of the drying compartment 111 by controlling the strength of the current of air under the control of the controller 10. This provides the effect of shaking the laundry provided in the clothes dryer with the blown air, so as to increase drying efficiency.

The effects of use of the clothes dryer using the LED light source having the above-described configuration according to the present invention will be described as follows.

First, in the state in which hangers, on which washed and spin-dried tops or bottoms are hung, are hung on the hanger rods 102 inside the drying compartment 111 of the clothes dryer 100 at regular intervals, the hinged door is closed, and the controller 10 turns on the LED light source modules 120 so as to dry the tops or bottoms using a quantity of heat caused by light radiated from the LED light source modules.

In the state in which the hinged door 101 is closed, the plurality of LED light source modules 120 installed under the drying compartment 111 radiates light upwards so as to dry clothes using the radiated light corresponding to 5700$k$ sunlight. Here, heat conducted to the heat sinks 121 of the LED light source modules 120 is guided to the first passages 131 of the air circulation parts 130 through driving of the radiation fans 122.

Air including the heat flowing into the first passages 131 is naturally introduced into the first passages 131 together with external air from below the main body 100, and such hot air is supplied to the inside of the drying compartment 111 by the air blowing fans 132 arranged at the same interval in the first passages 131 so as to maximize drying of the laundry.

That is, the hot air inhaled into the first passages 131 is circulated to the inside of the drying compartment 111 through the blow holes 133 by the air blowing fans 132, thus assisting drying of the laundry.

The air sterilization part 140 provided between the first passages 131 allows humid air generated by drying of the laundry inside the drying compartment to be inhaled into the second passage 141 through the first through holes 142, and simultaneously sterilizes the air using light radiated from the UV LEDs 143 installed in the air sterilization part 140.

As the humid air introduced into the second passage 141 moves upwards along the second passage 141, moisture is absorbed by the ceramic filters 144 arranged at the same interval.

Since a process of inhaling the humid air from the hollows and the surfaces of the ceramic filters 144, sufficiently absorbing moisture from the humid air while passing through the ceramic filters 144, and drying the moisture using hot air passing by the ceramic filters 144 is repeated in the above state, the clothes dryer according to the present invention may dry clothes through warm air circulation without requiring discharge of condensate water generated via a heat exchanger, i.e., separately collecting water, like the conventional dehumidification function.

Then, the air passes through the air discharge part 150 provided in the ceiling of the main body 110 through the second passage 141, and is discharged to the outside via the third through holes 155 through the exhaust fan 156 installed in the air discharge part 150.

The air introduced into the air discharge part 140 is sensed by the humidity sensor 153 via the third passage 151, a signal generated due to sensing of the air is transmitted to the controller 10, and the controller operates the above-described LED light source modules, the radiation fans, the air blowing fans, the UV LEDs and the exhaust fan so as to dry the clothes until the humidity inside the drying compartment indicating the dried state thereof reaches a predetermined humidity value.

If the humidity inside the drying compartment is less than the predetermined humidity value, for example, 5%, it is regarded that all laundry is dried, and the controller stops driving of the above-described elements so that the clothes dryer is in a stop mode.

In the clothes dryer according to the present invention, when the above-described drying process is performed in the state in which the trouser ironing plate provided on the rear surface of the hinged door 101 is rotated to be far away from the rear surface of the hinged door 101, trousers hung on a hanger come into contact with the rear surface of the hinged door and then the trouser ironing plate 170 is pressed against the trousers, the trouser ironing effect is exhibited.

The trouser ironing plate 170 is formed of stainless steel, the long hole 171 formed in the midsection thereof in the length direction thereof, and, when the trousers are pressed by the trouser ironing plate, parts of the side surfaces of the trousers having sewing lines having a relatively large thickness due to folding are located in the long hole 171, the trouser ironing plate 170 may be pressed against other parts of the side surfaces of the trousers, and thus, the trousers may be efficiently ironed.

The laundry drying compartment of the main body 110 minimizes temperature loss of conducted heat due to light radiation by the LED light source modules 120 because the inner walls of the drying compartment are formed of stainless steel (SUS), and the illumination lamps 154 installed around the humidity sensor 153 are turned on and radiate light to the inside of the drying compartment 111 through the second through holes 152 when the hinged door 101 is opened, and are turned off when the hinged door 101 is closed so as to conveniently manage and handle laundry inside the drying compartment.

Further, the plurality of air blowing fans 132 of the air circulation parts 130 according to the present invention, which is driven at a relatively low speed so as to have an air flow, shakes off clothes through control of the strength of the current of air blown by the air blowing fans 132 through control set by the controller 10, and thereby, may not only increase the drying effect but also efficiently remove dust from the clothes.

DESCRIPTION OF REFERENCE NUMERALS OR SYMBOLS

10: controller
100: clothes dryer
101: hinged door
102: hanger rod
110: main body
111: drying compartment
112: light source installation part
120: LED light source module
121: heat sink
122: radiation fan
130: air circulation part
130$a$: partition wall
131: first passage 132: air blowing fan
133: blow hole
140: air sterilization part
140b: sealing plate
141: second passage
142: first through hole
143: UV LED
144: ceramic filter
145: bracket
150: air discharge part
151: third passage
152: second through hole
153: humidity sensor
154: illumination lamp
155: third through hole
156: exhaust fan
160: support tray
161: perforated part
170: trouser ironing plate
171: long hole

The invention claimed is:

1. A clothes dryer using an LED light source, comprising:
a main body formed as a rectangular body, and provided with a hinged door provided on a front surface of the main body, a laundry drying compartment having hanger rods provided horizontally in upper and lower portions thereof inside the main body, a light source installation part provided under the laundry driving compartment, and a controller provided on one side of the front surface of the main body;
a plurality of LED light source modules installed under the drying compartment and configured to radiate light upwards so as to dry laundry using the radiated light;
air circulation parts provided with first passages formed on both sides of an inner rear surface of the drying compartment so as to communicate with the light source installation part, and a plurality of air blowing fans and a plurality of blow holes arranged inside the passages so as to perform air circulation and configured to guide air to an inside of the drying compartment through the light source installation part and the first passages;
an air sterilization part provided with a second passage formed between the first passages of the air circulation parts so as to be divided from the first passages by partition walls, a plurality of first through holes provided in the second passage, UV LEDs configured to radiate light to the drying compartment and air introduced thereinto so as to sterilize the air, and a plurality of ceramic filters configured to absorb moisture from the introduced air, the UV LEDs and the ceramic filters being installed at positions of the first through holes inside the air sterilization part; and
an air discharge part provided with a third passage configured to extend from an upper part of the second passage to an inside of a ceiling at an upper part of the drying compartment, a plurality of second through holes formed in the third passage so as to communicate with the drying compartment, a humidity sensor configured to measure humidity inside the second passage and the drying compartment, illumination lamps configured to illuminate the inside of the drying compartment depending on opening and closing of the hinged door, the humidity sensor and the illumination lamps being provided on the second through holes, a plurality of third through holes formed through one side of the third passage, and an exhaust fan provided on the third through holes so as to discharge air to an outside of the main body.

2. The clothes dryer according to claim 1, wherein the plurality of ceramic filters is provided in a form of a hollow block so as to have a moisture absorption area, and is arranged and fixedly installed at regular intervals by brackets.

3. The clothes dryer according to claim 1, wherein a support tray provided with a perforated part formed therethrough so as to transmit light is detachably installed on the LED light source modules.

4. The clothes dryer according to claim 1, wherein the air blowing fans provided in the first passages blow air to the inside of the drying compartment by controlling a strength of a current of air under control of the controller.

5. The clothes dryer according to claim 1, wherein each of the plurality of LED light source modules comprises a radial heat sink, and a radiation fan provided under the heat sink and configured to blow air so as to radiate heat generated from the heat sink.

6. The clothes dryer according to claim 1, wherein a thin stainless steel plate for heat reflection is added to the inside of the drying compartment of the main body and an inner surface of the hinged door.

7. The clothes dryer according to claim 1, wherein a trouser ironing plate formed of stainless steel to iron trousers is rotatably provided on a rear surface of the hinged door.

* * * * *